United States Patent [19]
Cossin

[11] 4,100,805
[45] Jul. 18, 1978

[54] SETTLING BASIN SAMPLER

[76] Inventor: George E. Cossin, Comiran Consulting Engineers, Soraya Ave., No. 1 Kouchen Mojdehi, Tehran, Iran

[21] Appl. No.: 790,274

[22] Filed: Apr. 25, 1977

[51] Int. Cl.² .............................................. G01N 1/14
[52] U.S. Cl. ................................................. 73/421 B
[58] Field of Search .......... 73/421 R, 421 B, 425.4 R, 73/425.6

[56] References Cited
U.S. PATENT DOCUMENTS
1,474,807  11/1923  Yetman et al. ................. 73/425.4 R Primary Examiner—S. Clement Swisher
Attorney, Agent, or Firm—Burton, Parker & Schramm

[57] ABSTRACT

A settling basin sampler comprises a column adapted to be supported on the bottom of the basin in a vertical position and having a plurality of valves supported thereon for vertical adjustable positioning to vary the depth of the sample drawn from the basin, a control rod extends parallel to the column and is connected to each valve for simultaneously opening and closing the valves, and sample receiving means are connected to each valve for receiving samples for fluid drawn from the basin at the various depths of the valves.

8 Claims, 3 Drawing Figures

SETTLING BASIN SAMPLER

FIELD OF INVENTION

This invention relates to samplers for settling basins and the like.

BACKGROUND OF THE INVENTION

Heretofore it has been the practice to sample fluids in settling basins at the surface to obtain a count on the suspended solids at the surface. Heretofore most settling basins are filled constantly and spill over an outlet weir at the far discharge end and when the basin is full of solids to a pre-determined depth, the liquid is drawn off and the solids removed and the process continued.

Improvements in settling basin technology and the impact of environmental considerations have led to development of new processes whereby the basin will be filled, held for settling, sampled at various depths, and then emptied from the top down so as to hold most of the suspended solids in check. As a result of this new approach to the treatment of fluids in settling basins, the need has arisen for a different type of sampling device, namely a device which is capable of sampling the fluid at varying depths from its surface to the bottom of the basin. Prior art devices of which I am aware do not have the capability of sampling the fluid at varying depths within the settling basin, only at the surface.

SUMMARY OF THE INVENTION

My invention comprises a multiple sampler having a vertical column adapted to be placed in any desired location in the settling basin to be supported at its lower end on the bottom of the basin and having a plurality of valves arranged in spaced apart relation along its vertical extent with each valve having an inlet port and an outlet port with the latter connected to means for receiving the collected sample. A control rod extends vertically parallel to the column and is connected to the valves and when shifted to one position will open the valves for establishing communication between the sample receiving means and the fluid in the basin at the depth of each valve and when shifted to another position will block communication between fluid in the basin and the sample receiving means. The column is desirably provided with means at its upper end facilitating manual placement or removal of the sampler in the basin.

BRIEF DESCRIPTION OF PREFERRED EMBODIMENT

Figure 1:
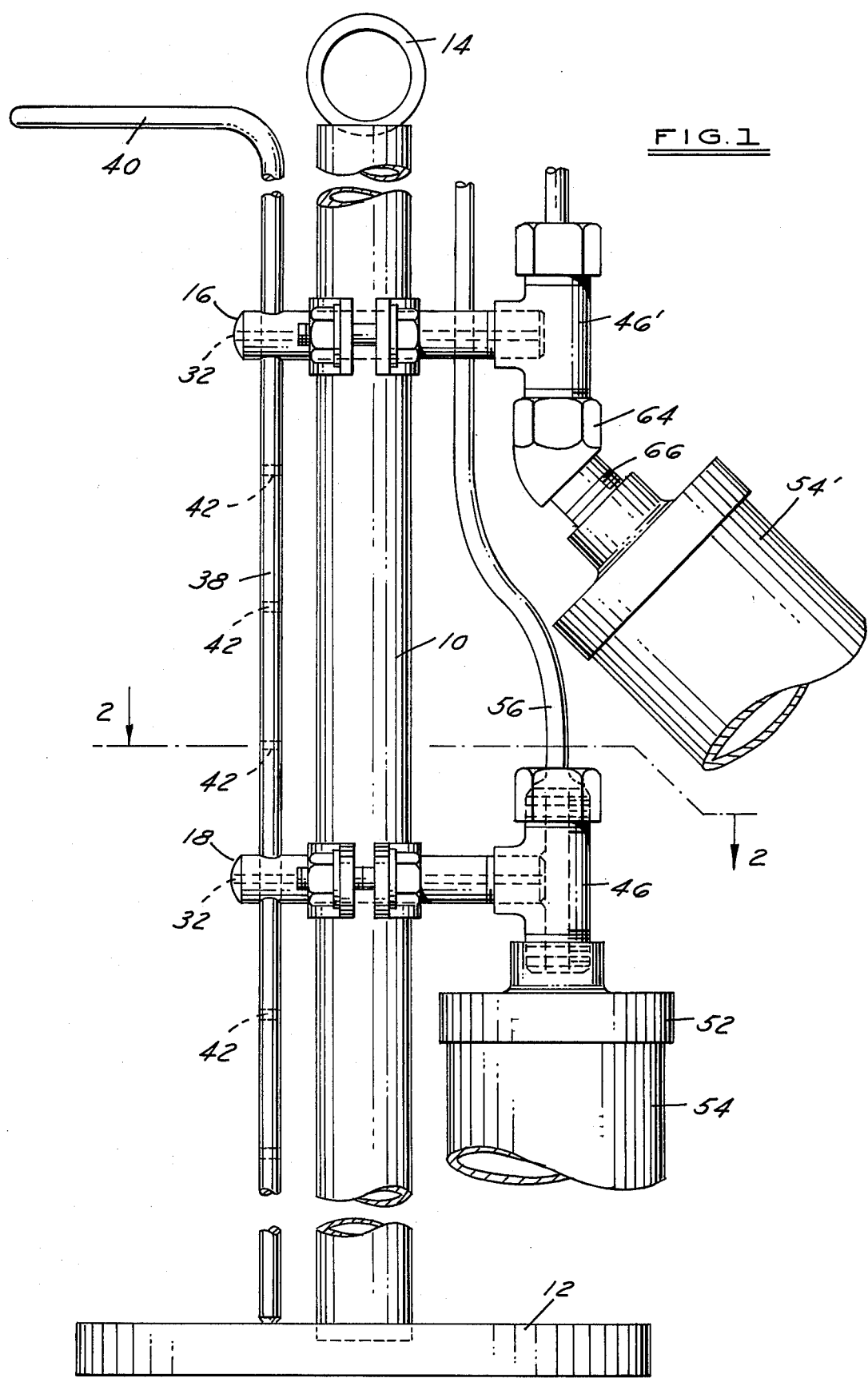
FIG. 1 is a side elevation of a sampler embodying my invention showing two representative valves and sample receiving means.

As shown in the drawings an embodiment of my invention includes an elongated column 10 having at its lower end a base member 12 secured to the column to support it in an upright or vertical position within the settling basin (not shown), the base member 12 sitting on the bottom of the basin. The column will extend up through the fluid in the basin and above the surface thereof. At the upper end of the column are means for enabling manual placement in and removal of the column from the settling basin, such means comprising a ring 14 secured to the column. The column is preferably formed of a lightweight non-corrosive material and is of cylindrical cross-section.

Figure 2:
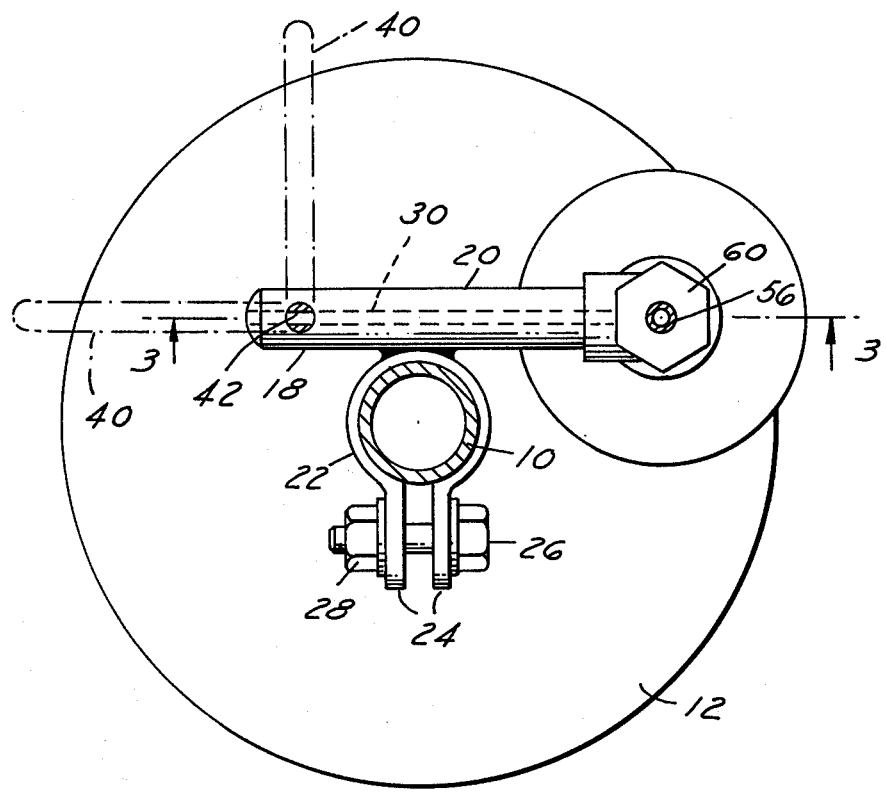
FIG. 2 is a cross-sectional view taken substantially on the line 2—2 of FIG. 1.
Figure 3:
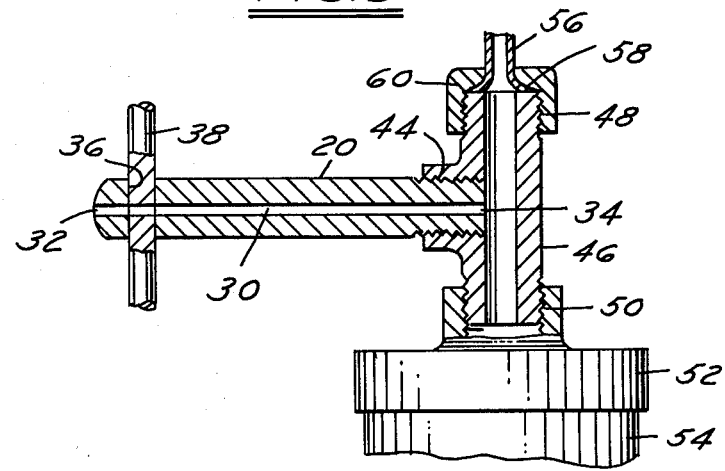
FIG. 3 is a cross-sectional view taken substantially on the line 3—3 of FIG. 2.

Mounted on the column in vertically spaced apart relation, for vertically adjustable positioning, are a plurality of valves, two of which are shown in FIG. 1 at 16 and 18. As shown in FIGS. 2 and 3, each valve includes a body portion 20 having a clamp 22 adapted to embrace the column with flanges 24 being disposed in spaced relation for reception therethrough of a bolt or the like 26 having nut means 28 thereon which when tightened will urge the flanges 24 together to tightly grip the clamp about the column 10 and thereby lock the valve at the position selected by the technician.

The valve body 20 of each valve includes a longitudinal passageway 30 extending between an inlet port 32 at one end of the body and an outlet port 34 at the opposite end of the body. Extending transversely through the valve body 20 in a vertical direction adjacent the inlet port 32 and intersecting the passageway 30 is a control rod receiving bore or passage 36.

A control rod 38 extends parallel to the column 10 with its lower end resting on the base member 12 to support the rod in the position shown. The upper end of the rod is provided with a laterally extending actuating portion 40 for facilitating manual shifting, i.e., rotation of the rod, above the surface of the fluid in the settling basin, and also indicating to the technician the rotated position of the rod relative to the column. The control rod is provided with a plurality of transversely extending longitudinally spaced apart through apertures 42.

The valves are intended to be adjustably positioned on the column so that one of the through apertures in the rod is disposed within each valve body in alignment with the longitudinal passageway 30. In setting up the sampler, the technician may readily align an aperture in the rod with any given valve by inserting a tapered pin or the like (not shown) through the inlet port 32 and into the passageway 30 and through aperture 42 in the rod and while the pin is in such position the nut 28 is tightened to secure the valve in proper position. The pin is then withdrawn from the valve.

It is intended that a plurality of such valves be provided on the column at vertically spaced positions corresponding to the depth of the fluid samples desired. With the control rod in the position shown in FIG. 1, fluid may enter each valve through the inlet ports 32 and enter the passageway 30 in the valve bodies.

At the opposite end of the valve bodies from the inlet port and in surrounding relation to the outlet port, the valve body is externally threaded as at 44 to receive thereon a Tee 46 externally threaded at ends 48 and 50. To end 50 may be threadedly connected the cap 52 of a sample receiving container 54. The container comprises a hollow cylindrical vessel closed at its lower end (not shown). The interior of the container communicates with the interior of the Tee through the cap 52.

The threaded end 48 of the Tee communicates with a vent tube 56, the upper end of which is in communication with atmospheric pressure air above the settling basin. If desired the tube 56 may be essentially rigid and supported by the Tee in a vertically upwardly extending position parallel to the column with the upper end of the tube terminating adjacent the lifting ring 14. The lower end of the tube 56 is flared as at 58 and retained against the end of the Tee by a coupling nut 60.

One such sample receiving vessel is associated with each valve as shown in FIG. 1. The vessels may be angled outwardly and downwardly away from the column to avoid interference of closely adjacent vessels and for this purpose the vessel 54' shown in FIG. 1 is connected to the Tee 46' by a 45° elbow 64 and short nipple 66.

In using the multiple sampler, the technician will turn the control rod to block the passageways through the valves and then lower the sampler into the settling basin such that the member 12 rests on the bottom and the column 10 extends vertically up above the surface of the basin fluid. After the disturbance of the fluid created by the insertion of the sampler has quieted down the control rod 38 is rotated by grasping the portion 40 and moving it to the position shown in FIG. 1. Fluid then enters the vessels 54 and 54' (as well as any other vessels which may be similarly connected to the column) and after sufficient time has passed so that a fair sample has been gathered the control rod is rotated to block the passageways 30 in the valves and the sampler is removed from the settling basin. The vessels 54 and 54' may then be removed from the sampler by simply unscrewing them. They are suitably labeled or otherwise identified by the technician as to the depth at which the drawn-off sample in each was obtained and the necesssary testing of the samples thereafter accomplished in the usual fashion.

While one control rod and only two valves and sample vessels have been shown, it is to be understood that additional valves may be mounted on the column in different angular orientation to those shown and additional control rods as needed or desired similarly provided so that a plurality of control rods and a considerable number of valves and sampler vessels may be provided on one column.

In practice the through apertures 42 may be at any desired location. Usually, however, the depth spacing for the sample selection is at 12-inch intervals but this may be varied in accordance with the depth and area of the settling basin and the settling time of the suspended solids.

In the event it is not desired to repeatedly immerse and remove the sampler from the settling basin, but rather to leave it in place for extended periods and take more or less continuous samples from the settling basin of the fluid at varying depths, the sampler vessels may be removed from the Tees 46 and the lower ends of the Tees closed by an internally threaded cap. The tube 56 may in turn be extended to a sampling device either at the surface or at a remote location adjacent the basin with means provided (not shown) for creating a partial vacuum on the lines 56 to cause the fluid to be drawn therethrough to the sampling device. In this fashion continuous samples may be taken of the fluid at various depths in the basin. The valve control rod 38 in this instance, could be left such that its through apertures are in alignment with the passageways in the valves, or it could be rotated to block the passageways when samples were not being drawn off.

What is claimed is:

1. A multiple sampler for settling basins and the like comprising, in combination:
   an elongated column,
   means for supporting the column in a vertical position in the fluid in the settling basin,
   a plurality of valves on the column at vertically spaced apart locations each having an inlet port exposed to fluid in the basin at the depth of the valve and an outlet port,
   individual containers removably connected to the outlet port of each valve for individually receiving fluid admitted through the valve, and
   means operable from above the surface of fluid in the basin for opening and closing the valves.

2. The invention defined by claim 1 wherein said valves are supported on the column for longitudinal adjustment therealong to vary the spacing therebetween and the depth of the sample collected.

3. A multiple sampler for settling basins and the like comprising, in combination:
   an elongated column,
   means for supporting the column in a vertical position in the fluid in the settling basin,
   a plurality of valves on the column at vertically spaced apart locations each having an inlet port exposed to fluid in the basin at the depth of the valve and an outlet port,
   sample receiving means connected to the outlet port of each valve for individually receiving fluid admitted through the valve,
   means operable from above the surface of fluid in the basin for opening and closing the valves,
   each valve including a valve body having a horizontally extending passage communicating with said ports and a vertically extending bore intersecting the passage, and
   said means for opening and closing the valves comprising a control rod extending parallel to the column and through said bores with a transverse through aperture in the rod disposed in each valve body alignable with the horizontal passage therein for permitting or preventing fluid flow through the passage on shifting the rod.

4. A multiple sampler for settling basins and the like comprising, in combination:
   an elongated column,
   means for supporting the column in a vertical position in the fluid in the settling basin,
   a plurality of valves on the column at vertically spaced apart locations each having an inlet port exposed to fluid in the basin at the depth of the valve and an outlet port,
   sample receiving means connected to the outlet port of each valve for individually receiving fluid admitted through the valve,
   means operable from above the surface of fluid in the basin for opening and closing the valves,
   each valve including a laterally extending clamp releasably embracing the column for vertical adjustable positioning of the valves on the column to vary the depth of the fluid to be sampled, and
   a control rod extends parallel to the column and operatively connected to each valve for opening and closing the same and having a manual actuating portion at the upper end to facilitate operation of the rod.

5. A multiple sampler for settling basins and the like comprising, in combination:
   an elongated column,
   means for supporting the column in a vertical position in the fluid in the settling basin,
   a plurality of valves on the column at vertically spaced apart locations each having an inlet port exposed to fluid in the basin at the depth of the valve and an outlet port, sample receiving means including a plurality of flexible tubes with one end connected to the outlet port of each valve and also connectable to a source of sub-atmospheric pressure for individually withdrawing fluid admitted through the valve for sampling, and means for opening and closing the valves.

6. The invention defined by claim 1 wherein a vent line communicates with the outlet port of each valve and its container and is exposed to atmospheric pressure.

7. The invention defined by claim 1 wherein each valve includes a releasable clamping portion embracing the column for longitudinal adjustable positioning of the valves on the column to sample fluid at varying depths in the basin, a base member affixed to the lower end of the column for supporting the same in the basin, a control rod extending parallel to the column with its lower end resting on the base member and provided with a plurality of transverse through apertures with one of the apertures disposed in each valve for alignment with a passageway in the valve communicating with the inlet and outlet ports, and said rod being rotatable between a position wherein said apertures are aligned with the passageway in the valve and a position in which the apertures are transverse to the passageway and the rod blocks the same.

8. A portable multiple sampler for settling basins and the like comprising, in combination:

a lightweight elongated column, a base member at one end of the column for supporting the column in a vertical position on the bottom of the settling basin with the column extending up through and above the surface of fluid in the basin, means at the upper end of the column for manually lowering the column into the basin or raising the same therefrom, a plurality of valves arranged along the column at vertically spaced apart intervals, each valve having releasable clamping means embracing the column for adjustable positioning of the valves therealong, each valve having an inlet port exposed to fluid in the basin and an outlet port with a passageway communicating between the ports, a control rod extending parallel to the column through each valve and intersecting the said passageway therein, a through aperture in the control rod disposed within the valve for alignment when the rod is in on position with the said passageway therein, manual operating means at the upper end of the control rod for shifting the rod between positions aligning said apertures with the passageways in the valves and blocking the passageways in the valves, a plurality of closed containers with one connected to the outlet port of each valve, and vent means comprising a tube communicating at one end with the container and exposed at the opposite end to atmospheric pressure above the basin.

* * * * *